United States Patent [19]

Wick

[11] Patent Number: 4,521,535

[45] Date of Patent: Jun. 4, 1985

[54] 4-PYRIDONE-3-CARBOXYLIC ACID DERIVATIVES

[75] Inventor: Alexander E. Wick, Riehen, Switzerland

[73] Assignee: Hoffmann-La Roche Inc., Nutley, N.J.

[21] Appl. No.: 369,778

[22] Filed: Apr. 19, 1982

Related U.S. Application Data

[63] Continuation of Ser. No. 187,878, Sep. 17, 1980, abandoned, which is a continuation of Ser. No. 002,474, Jan. 10, 1979, abandoned.

[30] Foreign Application Priority Data

Jan. 18, 1978 [CH] Switzerland ............... 51278/78
Nov. 15, 1978 [CH] Switzerland ............... 11734/78

[51] Int. Cl.$^3$ ............... A61K 31/435; C07D 213/80
[52] U.S. Cl. ............... 514/222; 546/298;
514/233; 514/236; 514/241; 514/252; 514/256;
514/318; 514/334; 514/335; 514/336; 514/340;
514/341; 514/342; 514/343; 514/350; 544/58.6;
544/131; 544/215; 544/224; 544/333; 544/365;
546/193; 546/257; 546/261; 546/270; 546/275;
546/276; 546/277; 546/278; 546/279; 546/280;
546/281; 546/284

[58] Field of Search ............ 546/298, 270, 193, 261,
546/275, 276, 277, 278, 279, 280, 281, 284;
542/442; 424/266, 246, 248.53, 248.55, 249,
250, 251; 544/58.6, 131, 219, 224, 333, 365

[56] References Cited

U.S. PATENT DOCUMENTS 3,907,808  9/1975  Lesher et al. ............... 546/156 X
4,152,136  5/1979  Taylor ............... 71/90
4,278,798  7/1981  Wick ............... 546/298

OTHER PUBLICATIONS

Cammarata et al., J. Med. Chem., vol. 19, No. 6, (1976), pp. 739–748.
Darvas et al., Arznein-Forsch/Drug Res., 29(II), No. 9, (1979), pp. 1334–1339.
Kametani et al., J. Het. Chem., vol. 14, No. 1, (1977), pp. 477–482.
Johnstone et al., Australian J. Chem., vol. 11, (1958), pp. 564–565.
Adachi, Chemical Abstracts, vol. 72, (1970), 55,301r.
Agui et al., J. Het. Chem., vol. 12, (1975), pp. 1245–1254.

*Primary Examiner*—Richard L. Raymond
*Attorney, Agent, or Firm*—Jon S. Saxe; George M. Gould; Steve T. Zelson

[57] ABSTRACT

The invention relates to 4-pyridone-3-carboxylic acid derivatives, a process for the preparation thereof and pharmaceutical compositions containing same. The 4-pyridone-3-carboxylic acid derivatives are useful as antibacterial agents and/or as agents having a stimulating activity on the central nervous system.

5 Claims, No Drawings

4-PYRIDONE-3-CARBOXYLIC ACID DERIVATIVES

This is a continuation of application Ser. No. 187,878 filed Sept. 17, 1980, now abandoned, which is a continuation of application Ser. No. 002,474, filed Jan. 10, 1979, now abandoned.

BRIEF SUMMARY OF THE INVENTION

The 4-pyridone-3-carboxylic acid derivatives of the invention are compounds of the formula

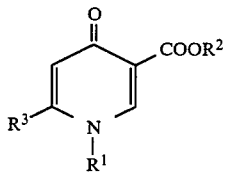

I wherein $R^1$, $R^2$ and $R^3$ are as hereinafter described, and salts thereof.

In another aspect, the invention relates to intermediates of the formula

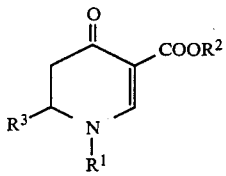

II wherein $R^1$, $R^2$ and $R^3$ are as hereinafter described.

DETAILED DESCRIPTION OF THE INVENTION

The 4-pyridone-3-carboxylic acid derivatives of the invention are compounds of the formula

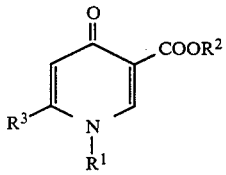

I wherein $R^1$ is $C_{1-8}$-alkyl, $C_{3-10}$-cycloalkyl, $C_{3-10}$-cycloalkyl$C_{1-6}$-alkyl, $C_{1-6}$-alkoxy or $C_{1-6}$-alkoxy-$C_{1-6}$-alkyl; $R^2$ is hydrogen or $C_{1-6}$-alkyl; $R^3$ is phenyl, phenethyl or styryl, which are optionally substituted by $R^4$, $R^5$ and/or $R^6$, or an aromatic heterocyclic 6-membered ring containing one or more N-atoms, which is linked via a ring C-atom and which is optionally substituted by $R^7$; $R^4$ and $R^5$ each, independently, are halogen, trifluoromethyl, hydroxy, $C_{1-6}$-alkoxy, $C_{1-6}$-alkylthio, $C_{1-6}$-alkyl, amino, acylamino, $C_{1-6}$-alkylamino, di-$C_{1-6}$-alkylamino, nitro or a 5-membered or 6-membered heterocycle linked via a ring N- or C-atom or $R^4$ and $R^5$, taken together, are $C_{1-6}$-alkylenedioxy; $R^6$ is $C_{1-6}$-alkoxy; and $R^7$ is halogen, hydroxy, $C_{1-6}$-alkoxy, $C_{1-6}$-alkylthio, $C_{1-6}$-alkyl, amino, $C_{1-6}$-alkylamino or di-$C_{1-6}$-alkylamino; provided that $R^2$ is $C_{1-6}$-alkyl when $R^1$ is methyl and simultaneously $R^3$ is phenyl, and salts thereof.

According to the process of the invention, the aforesaid 4-pyridone-3-carboxylic acid derivatives, that is, the compounds of formula I hereinbefore and their salts, are prepared by (a) dehydrogenating a 1,4,5,6-tetrahydronicotinic acid derivative of the formula

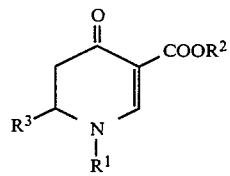

II wherein $R^1$, $R^2$ and $R^3$ are as previously described, in the 5,6-position, or (b) modifying a substituent $R^2$ and/or $R^3$ in a known manner within the definitions given earlier, and, if desired, converting a compound of formula I obtained into a salt, especially physiologically or pharmaceutically acceptable salts.

Exemplary of $C_{1-8}$-alkyl, which can be straight-chain or branched-chain, are methyl, ethyl, propyl, isopropyl, butyl, sec.butyl, tert.butyl, octyl or the like; methyl and ethyl are preferred. Exemplary of $C_{1-6}$-alkylenedioxy are methylenedioxy and ethylenedioxy and the like. Cyclopropyl is a preferred $C_{3-10}$-cycloalkyl. The term "halogen" includes fluorine, chlorine, bromine and iodine. Exemplary of aromatic heterocyclic 6-membered rings containing one or more N-atoms denoted by $R^3$ are 2-, 3- or 4-pyridyl, 3- or 4-pyridazyl, 2-, 4- or 5-pyrimidyl, 2- or 3-pyrazyl and the like. When $R^4$ and/or $R^5$ are a 5-membered or 6-membered heterocycle linked via a ring N- or C-atom, they can be, for example, a pyrrole, pyrroline, pyrrolidine, isoxazole, oxazole, thiophene, thiazole, pyrazole, imidazole, imidazoline, imidazolidine, triazole, oxadiazole, pyridine, piperidine, morpholine, piperazine, thiazine, pyridazine, pyrimidine, triazine or the like. The acyl group in an acylamino is preferably derived from an aliphatic carboxylic acid, such as, an acid containing 1–6 carbon atoms, for example, formic acid, acetic acid, propionic acid, or the like.

Compounds of formula I wherein $R^2$ is hydrogen form alkali metal, alkaline earth metal and ammonium salts, the latter being optionally substituted. When basic substituents are present in the molecule, the compounds of formula I form addition salts with physiologically or pharmaceutically compatible strong inorganic and organic acids, for example, hydrochloric acid, sulfuric acid, phosphoric acid, methanesulfonic acid, paratoluenesulfonic acid, and the like.

Preferred compounds of formula I are those wherein $R^1$ is ethyl or propyl, those wherein $R^2$ is hydrogen or methyl and those wherein $R^3$ is substituted phenyl, a substituent, especially a substituted amino or a nitrogen-containing heterocycle, in the 4-position of said phenyl is especially preferred.

The dehydrogenation of a 1,4,5,6-tetrahydronicotinic acid derivative of formula II in accordance with embodiment (a) of the process can be carried out according to known methods, conveniently with a substituted benzoquinone, such as, 2,3-dichloro-5,6-dicyano-1,4-benzoquinone (DDQ) or tetrachloro-1,4-benzoquinone (chloranil) in an inert organic solvent such as methylene chloride, toluene or dioxane and at a temperature in the range of from room temperature up to the reflux temperature of the mixture. In general, the dehydrogenation is carried out by adding a solution of the substituted benzoquinone dropwise to the solution of the 1,4,5,6-tetrahydronicotinic acid derivative, care being taken to use equimolar amounts. Where colorless starting materials are used, the end of the dehydrogenation can readily be detected by the appearance of a colored mixture. The product can be isolated from the mixture in the usual manner and can be purified, for example, by recrystallization or chromatography.

In accordance with embodiment (b) of the process, a substituent $R^2$ and/or $R^3$ can be modified in a known manner within the definitions given earlier.

Thus, for example, the carboxyl group ($R^2$=H) can be esterified or an ester group ($R^2$=$C_{1-6}$-alkyl) can be saponified. An amino group present on a substituent $R^3$ can be alkylated, a nitro group can be reduced to an amino group, a hydroxy group can be etherified, an alkoxy group can be cleaved or a halogen can be replaced by a different halogen or another functional group. Furthermore, a saturated heterocyclic substituent can be dehydrogenated if desired, a partially or completely unsaturated heterocycle can be hydrogenated or the styryl group can be hydrogenated to the phenethyl group without the basic structure common to all compounds provided by the invention thereby being altered.

The starting materials of formula II can be prepared, in accordance with the invention, by heating a 2-($R^1$-aminomethylene)-3-oxo-4-pentenoic acid derivative of the formula

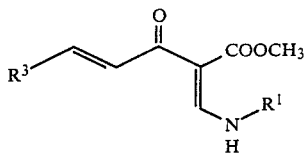

wherein $R^1$ and $R^3$ are as previously described, conveniently in an inert polar aprotic organic solvent such as, for example, dimethylformamide (DMF), dimethylsulfoxide (DMSO) or hexamethylphosphoric acid triamide. The solution is heated at a temperature in the range of from about 100° C. up to the reflux temperature for 1 to several hours, whereby ring closure to the 1,4,5,6-tetrahydronicotinic acid derivative of formula II occurs.

The 2-($R^1$-aminomethylene)-3-oxo-4-pentenoic acid derivatives of formula III can be obtained in a known manner in a multi-stage synthesis from aldehydes of the formula $R^3$—CHO.

The preparation of 1-ethyl-6-phenyl-4-oxo-1,4-dihydronicotinic acid from benzaldehyde is generically described in the Formula Scheme which follows and the preparation of 1-ethyl-6-(4-chlorophenyl)-4-oxo-1,4-dihydronicotinic acid and its methyl ester is described in detail in Example 1 hereinafter.

FORMULA SCHEME

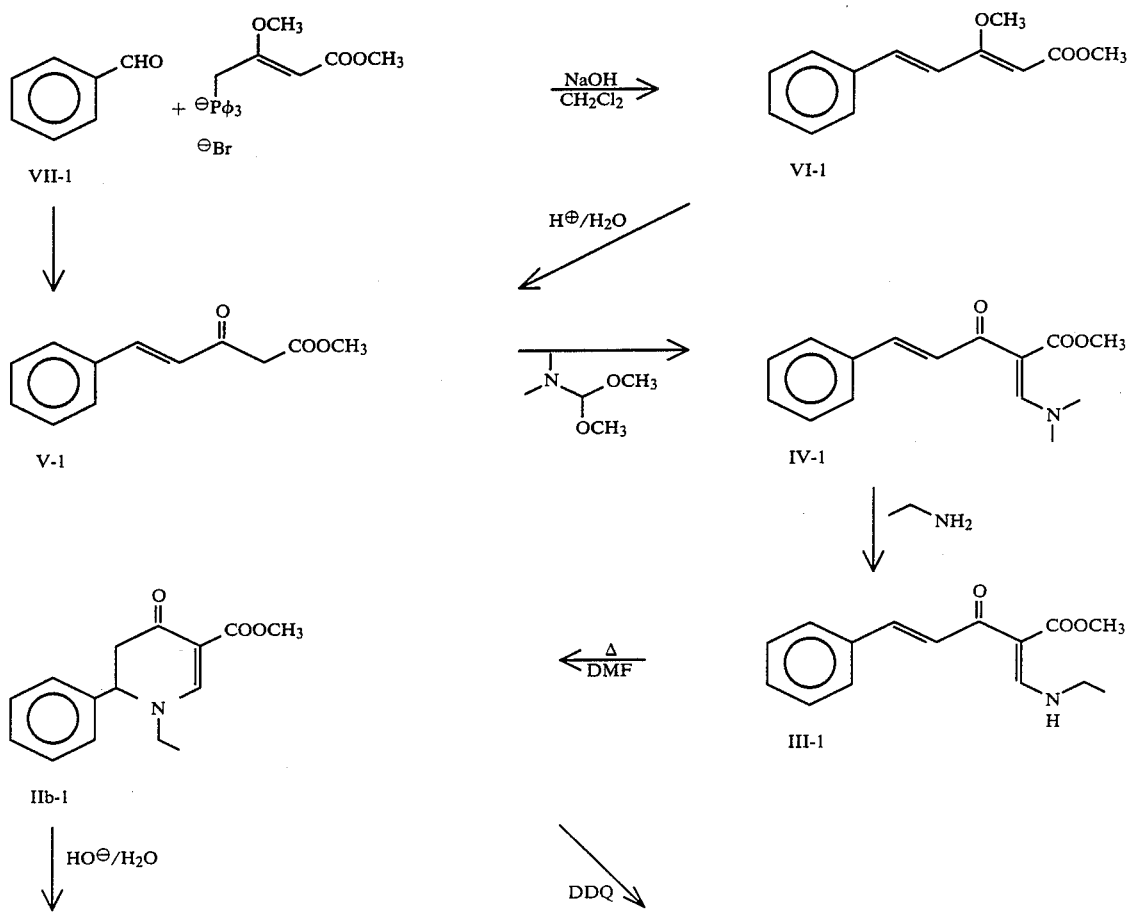

-continued
FORMULA SCHEME

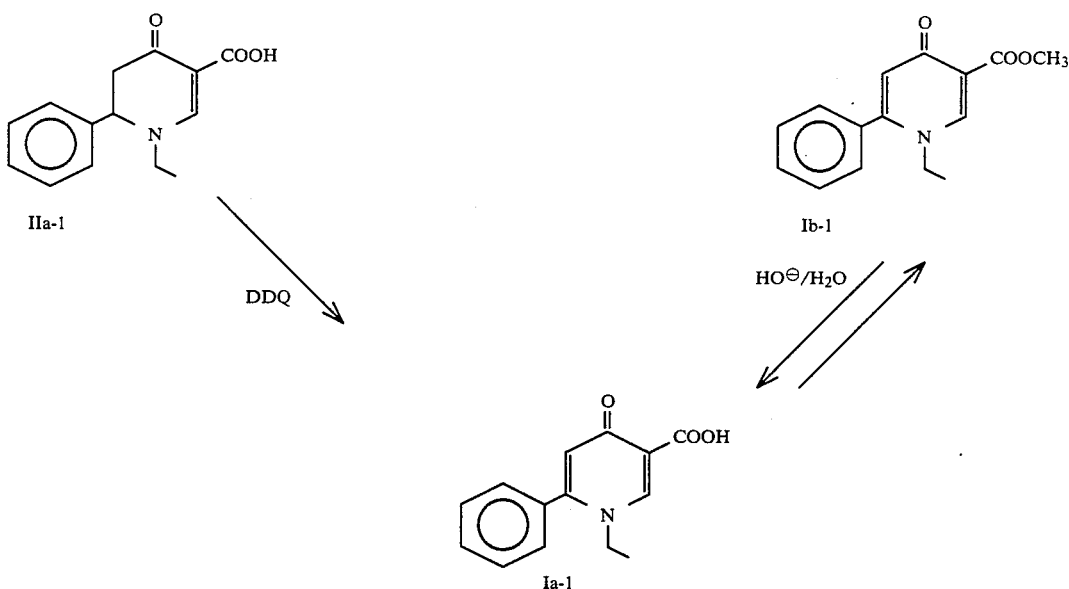

By varying the aldehyde of formula VII-1, the ester group of the triphenylphosphonium compound or the amine which is reacted with a compound of formula IV-1 to give a derivative of formula III-1, in principle all compounds in accordance with the present invention can be prepared in an analogous manner.

The 1,4,5,6-tetrahydronicotinic acid derivatives of formula II and the 2-($R^1$-aminomethylene)-3-oxo-4-pentenoic acid derivatives of formula III are novel and also form part of the present invention.

The compounds of formula I hereinbefore possess pharmacological activity. More specifically, the compounds of formula I possess antibacterial activity and-/or a stimulating activity on the central nervous system. Further, said compounds have low acute toxicities. Thus, for example, 1-ethyl-4-oxo-6-phenyl-1,4-dihydronicotinic acid has a substantially superior activity to nomifensin with about the same $LD_{50}$, and it shows advantage over d-amphetamine and d-methamphetamine by having a substantially lower $LD_{50}$ with about the same strong activity (see Table 1 hereinafter).

TABLE 1

| Compound | $LD_{50}$ | Turning rat test(1) minimum active dosage |
|---|---|---|
| 1-Ethyl-4-oxo-6-phenyl-1,4-dihydronicotinic acid | 300–600 p.o. | 1 |
| Nomifensin | 300–600 p.o. | 3 |
| d-Amphetamine ½ $H_2SO_4$ | 35 p.o., 14 i.v., 22 s.c. | 1 |
| d-Methamphetamine HCl | 9.5 i.v., 14 s.c. | 1 |

(1)Arch. int. Pharmacodyn. Ther. 217, 118–130 (1975)

With regard to the antibacterial activity of the compounds of formula I, they are especially suitable as therapeutic agents in urinary tract infections. Vis-a-vis known compounds having this indication, for example, nitrofurantoin, they possess an increased activity against specific causative organisms, such as, Escherichia coli (see Table 2 hereinafter). In view of their central nervous system stimulating activity the compounds of formula I can be used, for instance, as antidepressants.

TABLE 2

| | Escherichia coli | |
|---|---|---|
| Compound | in vitro MIC* μg/ml | in vivo (mouse) $ED_{50}$ mg/kg p.o. |
| Nitrofurantoin | 5 | >100 |
| 1-Ethyl-6-(4-methoxyphenyl)-4-oxo-1,4-dihydronicotinic acid | 2.5 | >100 |
| 1-Ethyl-6-(3,4-methylenedioxyphenyl)-4-oxo-1,4-dihydronicotinic acid | 2.5 | >100 |
| 1-Ethyl-6-(4-methylthiophenyl)-4-oxo-1,4-dihydronicotinic acid | 2.5 | 82 |
| 1-Ethyl-6-(4-pyrrolophenyl)-4-oxo-1,4-dihydronicotinic acid | 1.2 | 34 |
| 1-Ethyl-6-(4-pyrrolidinophenyl)-4-oxo-1,4-dihydronicotinic acid | 1.2 | 19 |
| 1-Ethyl-6-(4-dimethylaminophenyl)-4-oxo-1,4-dihydronicotinic acid | 0.6 | 8.8 |
| 1-Ethyl-6-(3-methyl-4-methylaminophenyl)-4-oxo-1,4-dihydronicotinic acid | 0.6 | 3.5 |

*Minimum Inhibitory Concentration

The 4-pyridone-3-carboxylic acid derivatives provided by the invention can therefore be used in the therapy and prophylaxis of infections, especially of bacterial infections, and for the stimulation of the central nervous system in the form of pharmaceutical preparations which provide for direct or delayed liberation of the active ingredient and which contain them in association with a carrier material. Such carrier material can be organic or inorganic inert carrier material suitable for oral, rectal or parenteral administration, for example, water, gelatin, gum arabic, lactose, starch, magnesium stearate, talc, vegetable oils, polyalkyleneglycols, petroleum jelly or the like. The pharmaceutical preparations can be made up in solid form, for example, as tablets, dragees, suppositories or capsules, in semisolid form, for example, as salves, or in liquid form, for example, as solutions, suspensions or emulsions. The pharmaceutical preparations may be sterilized and/or may contain adjuvants such as preserving, stabilizing, wetting or emulsifying agents, agents for flavor improvement, salts for varying the osmotic pressure or buffer substances.

The pharmaceutical preparations can be prepared in a known manner, namely, by mixing the active ingredient with non-toxic inert carrier materials suitable for therapeutic administration and finishing the resulting mixture into a suitable galenical form.

As dosage guidelines for the compounds of formula I as an antibacterial agent there can be considered an amount of 10–100 mg/kg, preferably about 50 mg/kg, body weight per day, and as an agent having an activity on the central nervous system there can be considered an amount of 100 µg–10 mg/kg.

The following Examples further illustrate the invention. All temperatures are stated in degrees Centigrade, unless otherwise mentioned.

EXAMPLE 1

Preparation of 1-ethyl-6-(4-chlorophenyl)-4-oxo-1,4-dihydronicotinic acid 3 g. of 1-ethyl-6-(4-chlorophenyl)-4-oxo-1,4,5,6-tetrahydronicotinic acid methyl ester were heated to 80° C. in 50 ml. of benzene and treated dropwise with a benzene solution of 4 g. of dichlorodicyanobenzoquinone (DDQ) until decolorization was no longer visible. The mixture was cooled and the crystalline material which thereby separated out was filtered off under suction.

The resulting material, a mixture of 1-ethyl-6-(4-chlorophenyl)-4-oxo-1,4-dihydronicotinic acid methyl ester with DDQ, was stirred with 20 ml. of 1N sodium hydroxide at room temperature for 30 minutes, the clear solution was diluted with 50 ml. of ice-water and cautiously acidified to pH 6.5 with 0.5-N hydrochloric acid. In so doing, the product separated in almost pure form. It was recrystallized from ethyl acetate. There were obtained 2.1 g. of 1-ethyl-6-(4-chlorophenyl)-4-oxo-1,4-dihydronicotinic acid having a melting point of 215°–217° C.

The starting material was prepared as follows:

14 g. of 4-chlorobenzaldehyde and 47 g. of [2-methoxy-3-(methoxycarbonyl)allyl]-triphenylphosphonium bromide were dissolved in 130 ml. of methylene chloride. 100 ml. of 50% aqueous hydroxide were allowed to flow into the resulting solution at room temperature while stirring well, a temperature increase being observed. The mixture was stirred for a further 20 minutes, poured on to ice and extracted with methylene chloride. The residue remaining after drying over sodium sulfate and evaporation of the solvent was crystallized from methanol, the mother liquor in hexane/ether (4:1 v/v) was filtered through a short silica gel column and the product crystallizing out from the eluate was combined with the main product. The total yield was 23.5 g. of pure 5-(4-chlorophenyl)-3-methoxy-2,4-pentadienecarboxylic acid methyl ester having a melting point of 69°–72° C.

23.5 g. of 5-(p-chlorophenyl)-3-methoxy-2,4-pentadienecarboxylic acid methyl ester dissolved in 250 ml. of dioxane were treated with 150 ml. of 0.1-N sulfuric acid and held at 100° C. for 3 hours. The mixture was cooled down, extracted with ethyl acetate, dried and crystallized by the addition of hexane. There were obtained 14.8 g. of 5-(4-chlorophenyl)-3-oxo-4-pentenoic acid methyl ester having a melting point of 78°–80° C.

14.8 g. of 5-(4-chlorophenyl)-3-oxo-4-pentenoic acid methyl ester were dissolved in 100 ml. of benzene and treated with N,N-dimethylformamide dimethylacetal. The red-brown colored solution was stirred at 60° C. for 30 minutes, solvent and excess reagent were removed and there was obtained 5-(4-chlorophenyl)-2-(dimethylaminomethylene)-3-oxo-4-pentenoic acid methyl ester in the form of a red-brown oil which was further processed in this form.

The oil obtained was dissolved in 50 ml. of benzene and stirred at room temperature for 30 minutes with 100 ml. of a saturated benzene solution of ethylamine. Thereafter, the solvent was removed and the residue was crystallized from ether/hexane. There were obtained 12.4 g. of 2-(ethylaminomethylene)-5-(4-chlorophenyl)-3-oxo-4-pentenoic acid methyl ester having a melting point of 78°–80° C.

5.2 g. of 2-(ethylaminomethylene)-5-(4-chlorophenyl)-3-oxo-4-pentenoic acid methyl ester in 50 ml. of dimethylformamide were held at 140°–150° C. for 3 hours. After removal of the solvent, there was obtained 1-ethyl-6-(4-chlorophenyl)-4-oxo-1,4,5,6-tetrahydronicotinic acid methyl ester in the form of a uniform oily residue.

In an analogous manner,
from benzaldehyde and propylamine there was obtained 4-oxo-6-phenyl-1-propyl-1,4-dihydronicotinic acid having a melting point of 153°–154° C.;
from benzaldehyde and isopropylamine there was obtained 1-isopropyl-4-oxo-6-phenyl-1,4-dihydronicotinic acid having a melting point of 215°–216° C.;
from benzaldehyde and butylamine there was obtained 1-butyl-4-oxo-6-phenyl-1,4-dihydronicotinic acid having a melting point of 119°–120° C.;
from benzaldehyde and tert.butylamine there was obtained 1-tert.butyl-4-oxo-6-phenyl-1,4-dihydronicotinic acid having a melting point of 295° C. (decomposition);
from benzaldehyde and octylamine there was obtained 1-octyl-4-oxo-6-phenyl-1,4-dihydronicotinic acid having a melting point of 62°–63° C.;
from benzaldehyde and cyclopropylmethylamine there was obtained 1-(cyclopropylmethyl)-4-oxo-6-phenyl-1,4-dihydronicotinic acid having a melting point of 177°–179° C.;
from benzaldehyde and cyclopropylamine there was obtained 1-cyclopropyl-4-oxo-6-phenyl-1,4-dihydronicotinic acid having a melting point of 180°–181° C.;
from benzaldehyde and cyclopentylamine there was obtained 1-cyclopentyl-4-oxo-6-phenyl-1,4-dihydronicotinic acid having a melting point of 188°–190° C.;
from benzaldehyde and cyclohexylamine there was obtained 1-cyclohexyl-4-oxo-6-phenyl-1,4-dihydronicotinic acid having a melting point of 257°–259° C.;
from benzaldehyde and 1-adamantylamine there was obtained 1-(1-adamantyl)-4-oxo-6-phenyl-1,4-dihydronicotinic acid having a melting point of 248° C. (decomposition);
from benzaldehyde and 2-methoxyethylamine there was obtained 1-(2-methoxyethyl)-4-oxo-6-phenyl-1,4-dihydronicotinic acid having a melting point of 144°–146° C.;

from benzaldehyde and methoxylamine there was obtained 1-methoxy-4-oxo-6-phenyl-1,4-dihydronicotinic acid having a melting point of 193°–194° C.;

from benzaldehyde and O-butyl-hydroxylamine there was obtained 1-butoxy-4-oxo-6-phenyl-1,4-dihydronicotinic acid having a melting point of 130°–132° C.;

from 3-nitrobenzaldehyde and ethylamine there was obtained 1-ethyl-6-(3-nitrophenyl)-4-oxo-1,4-dihydronicotinic acid having a melting point of 242°–243° C.;

from 3-aminobenzaldehyde and ethylamine there was obtained 1-ethyl-6-(3-aminophenyl)-4-oxo-1,4-dihydronicotinic acid having a melting point of 145°–146° C.;

from 4-(dimethylamino)-benzaldehyde and methoxylamine there was obtained 6-[4-(dimethylamino)-phenyl]-1-methoxy-4-oxo-1,4-dihydronicotinic acid having a melting point of 224° C. (decomposition);

from 4-(dimethylamino)-benzaldehyde and O-butyl-hydroxylamine there was obtained 1-butoxy-6-[4-(dimethylamino)-phenyl]-4-oxo-1,4-dihydronicotinic acid having a melting point of 155°–157° C.;

from 4-acetamido-benzaldehyde and ethylamine there was obtained 6-(4-acetamidophenyl)-1-ethyl-4-oxo-1,4-dihydronicotinic acid having a melting point of 237.5°–239° C.;

from 3-(trifluoromethyl)-benzaldehyde and ethylamine there was obtained 1-ethyl-6-[3-(trifluoromethyl)-phenyl]-4-oxo-1,4-dihydronicotinic acid having a melting point of 186°–188° C.;

from 4-(4-methylpiperazino)-benzaldehyde and ethylamine there was obtained 1-ethyl-6-[4-(4-methylpiperazino)-phenyl]-4-oxo-1,4-dihydronicotinic acid having a melting point of 246°–248° C.; and from p-methoxycinnamaldehyde and ethylamine there was obtained 1-ethyl-6-(p-methoxystyryl)-4-oxo-1,4-dihydronicotinic acid having a melting point of 237°–238° C.

EXAMPLE 2

Preparation of 1-ethyl-6-(4-chlorophenyl)-4-oxo-1,4-dihydronicotinic acid 800 mg. of 1-ethyl-6-(4-chlorophenyl)-4-oxo-1,4,5,6-tetrahydronicotinic acid in 20 ml. of benzene were treated dropwise at 80° C. with a solution of 1.5 g. of dichlorodicyanobenzoquinone (DDQ) in 30 ml. of benzene until the solution was no longer decolorized. The mixture was cooled down, the precipitate was filtered off under suction, dissolved in 20 ml. of 1N sodium hydroxide and the solution was cautiously acidified to pH 6.5 with cold 0.5-N hydrochloric acid. The separated colorless product was washed with water and then with ether. There was obtained 0.7 g. of 1-ethyl-6-(4-chlorophenyl)-4-oxo-1,4-dihydronicotinic acid having a melting point of 214°–215° C.

The starting material was obtained by dissolving 1.85 g. of 1-ethyl-6-(4-chlorophenyl)-4-oxo-1,4,5,6-tetrahydronicotinic acid methyl ester (prepared as described in Example 1) in 10 ml. of dioxane and 10 ml. of methanol and heating the solution under reflux for 3 hours in the presence of 20 ml. of 1-N sodium hydroxide. The mixture was cooled down, acidified with 0.5-N hydrochloric acid, the separated crystals were filtered off under suction and recrystallized from methanol/ether. Yield 1.3 g.; melting point 142°–144° C.

EXAMPLE 3

Preparation of 1-ethyl-4-oxo-6-phenyl-1,4-dihydronicotinic acid

In a manner analogous to that described in Examples 1 and 2, from benzaldehyde there was obtained 2-(ethylaminomethylene)-3-oxo-5-phenyl-4-pentenoic acid methyl ester, melting point 92°–94° C., this was cyclized and saponified to give 1-ethyl-4-oxo-6-phenyl-1,4,5,6-tetrahydronicotinic acid, melting point 148°–150° C., and this was subsequently dehydrogenated to give 1-ethyl-4-oxo-6-phenyl-1,4-dihydronicotinic acid, melting point 166°–167° C.

EXAMPLE 4

Preparation of 1-ethyl-6-[4-dimethylamino)-phenyl]-4-oxo-1,4-dihydronicotinic acid In a manner analogous to that described in Example 1, from 4-(dimethylamino)benzaldehyde there was obtained 2-(ethylaminomethylene)-5-[4-(dimethylamino)-phenyl]-3-oxo-4-pentenoic acid methyl ester, melting point 129°–130° C., this was cyclized to give 1-ethyl-6-[4-(dimethylamino)-phenyl]-4-oxo-1,4,5,6-tetrahydronicotinic acid methyl ester, melting point 85°–87° C., and this was dehydrogenated and saponified to give 1-ethyl-6-[4-(dimethylamino)-phenyl]-4-oxo-1,4-dihydronicotinic acid, melting point 258°–259° C.

EXAMPLE 5

Preparation of 1-ethyl-6-[3-methyl-4-(dimethylamino)-phenyl]-4-oxo-1,4-dihydronicotinic acid In a manner analogous to that described in Example 1, from 3-methyl-4-(dimethylamino)-benzaldehyde there was obtained 2-(ethylaminomethylene)-5-[3-methyl-4-(dimethylamino)-phenyl]-3-oxo-4-pentenoic acid methyl ester, melting point 98°–100° C., this was cyclized to give 1-ethyl-6-[3-methyl-4-(dimethylamino)-phenyl]-4-oxo-1,4,5,6-tetrahydronicotinic acid methyl ester, this was dehydrogenated to give 1-ethyl-6-[3-methyl-4-(dimethylamino)-phenyl]-4-oxo-1,4-dihydronicotinic acid methyl ester, melting point 132°–134° C., and this was saponified to give 1-ethyl-6-[3-methyl-4-(dimethylamino)-phenyl]-4-oxo-1,4-dihydronicotinic acid, melting point 160°–162° C.

EXAMPLE 6

Preparation of 1-ethyl-6-(4-pyrrolophenyl)-4-oxo-1,4-dihydronicotinic acid

In a manner analogous to that described in Examples 1 and 2, from 4-pyrrolobenzaldehyde there was obtained 2-(ethylaminomethylene)-3-oxo-5-(4-pyrrolophenyl)-4-pentenoic acid methyl ester, melting point 119°–121° C., this was cyclized and saponified to give 1-ethyl-6-(4-pyrrolophenyl)-4-oxo-1,4,5,6-tetrahydronicotinic acid and this was subsequently dehydrogenated to give 1-ethyl-6-(4-pyrrolophenyl)-4-oxo-1,4-dihydronicotinic acid, melting point above 300° C.

EXAMPLE 7

Preparation of 1-ethyl-6-(4-methoxyphenyl)-4-oxo-1,4-dihydronicotinic acid

In a manner analogous to that described in Examples 1 and 2, from 4-methoxybenzaldehyde there was obtained 2-(ethylaminomethylene)-3-oxo-5-(4-methoxyphenyl)-4-pentenoic acid methyl ester, this was cyclized and saponified to give 1-ethyl-6-(4-methoxyphenyl)-4-oxo-1,4,5,6-tetrahydronicotinic acid, melting point 173°–174° C., and this was subsequently dehydrogenated to give 1-ethyl-6-(4-methoxyphenyl)-4-oxo-1,4-dihydronicotinic acid, melting point 215°–217° C.

EXAMPLE 8

Preparation of 1-cyclopropyl-6-(4-methoxyphenyl)-4-oxo-1,4-dihydronicotinic acid In a manner analogous to that described in Examples 1 and 2, from 4-methoxybenzaldehyde there was obtained 2-(cyclopropylaminomethylene)-5-(4-methoxyphenyl)-3-oxo-4-pentenoic acid methyl ester, melting point 125°–127° C., this was cyclized and saponified to give 1-cyclopropyl-6-(4-methoxyphenyl)-4-oxo-1,4,5,6-tetrahydronicotinic acid, melting point 137°–139° C., and this was subsequently dehydrogenated to give 1-cyclopropyl-6-(4-methoxyphenyl)-4-oxo-1,4-dihydronicotinic acid, melting point 159°–161° C.

EXAMPLE 9

Preparation of 1-ethyl-6-(3,4-dimethoxyphenyl)-4-oxo-1,4-dihydronicotinic acid

In a manner analogous to that described in Examples 1 and 2, from 3,4-dimethoxy-benzaldehyde there was obtained 2-(ethylaminomethylene)-5-(3,4-dimethoxyphenyl)-3-oxo-4-pentenoic acid methyl ester, this was cyclized to give 1-ethyl-6-(3,4-dimethoxyphenyl)-4-oxo-1,4,5,6-tetrahydronicotinic acid methyl ester, melting point 134°–135° C., this was saponified to give 1-ethyl-6-(3,4-dimethoxyphenyl)-4-oxo-1,4,5,6-tetrahydronicotinic acid, melting point 182°–183° C., and this was subsequently dehydrogenated to give 1-ethyl-6-(3,4-dimethoxyphenyl)-4-oxo-1,4-dihydronicotinic acid, melting point 232°–234° C.

EXAMPLE 10

Preparation of 1-ethyl-6-(3,4-methylenedioxyphenyl)-4-oxo-1,4-dihydronicotinic acid In a manner analogous to that described in Examples 1 and 2, from 3,4-methylenedioxy-benzaldehyde there was obtained 2-(ethylaminomethylene)-5-(3,4-methylenedioxyphenyl)-3-oxo-4-pentenoic acid methyl ester, melting point 124°–125° C., this was cyclized and saponified to give 1-ethyl-6-(3,4-methylenedioxyphenyl)-4-oxo-1,4,5,6-tetrahydronicotinic acid, melting point 173°–175° C., and this was subsequently dehydrogenated to give 1-ethyl-6-(3,4-methylenedioxyphenyl)-4-oxo-1,4-dihydronicotinic acid, melting point 269°–270° C.

The last-mentioned acid was converted in a manner known per se into 1-ethyl-6-(3,4-methylenedioxyphenyl)-4-oxo-1,4-dihydronicotinic acid methyl ester, having a melting point of 183°–185° C.

EXAMPLE 11

Preparation of 1-cyclopropyl-6-(3,4-methylenedioxyphenyl)-4-oxo-1,4-dihydronicotinic acid In a manner analogous to that described in Examples 1 and 2, from 3,4-methylenedioxy-benzaldehyde there was obtained 2-(cyclopropylaminomethylene)-5-(3,4-methylenedioxyphenyl)-3-oxo-4-pentenoic acid methyl ester, melting point 158°–160° C., this was cyclized and saponified to give 1-cyclopropyl-6-(3,4-methylenedioxyphenyl)-4-oxo-1,4,5,6-tetrahydronicotinic acid, melting point 122°–124° C., and this was subsequently dehydrogenated to give 1-cyclopropyl-6-(3,4-methylenedioxyphenyl)-4-oxo-1,4-dihydronicotinic acid, melting point 211°–212° C.

EXAMPLE 12

Preparation of 1-ethyl-4-oxo-6-(3,4,5-trimethoxyphenyl)-1,4-dihydronicotinic acid In a manner analogous to that described in Examples 1 and 2, from 3,4,5-trimethoxy-benzaldehyde there was obtained 2-(ethylaminomethylene)-3-oxo-5-(3,4,5-trimethoxyphenyl)-4-pentenoic acid methyl ester in the form of an oil, this was cyclized to give 1-ethyl-4-oxo-6-(3,4,5-trimethoxyphenyl)-1,4,5,6-tetrahydronicotinic acid methyl ester and this was subsequently dehydrogenated and saponified to give 1-ethyl-4-oxo-6-(3,4,5-trimethoxyphenyl)-1,4-dihydronicotinic acid, melting point 200°–201° C.

EXAMPLE 13

Preparation of 1-ethyl-6-(4-methylthiophenyl)-4-oxo-1,4-dihydronicotinic acid

In a manner analogous to that described in Examples 1 and 2, from 4-(methylthio)-benzaldehyde there was obtained 2-(ethylaminomethylene)-5-(4-methylthiophenyl)-3-oxo-4-pentenoic acid methyl ester, this was cyclized and saponified to give 1-ethyl-6-(4-methylthiophenyl)-4-oxo-1,4,5,6-tetrahydronicotinic acid, melting point 173°–174° C., and this was subsequently dehydrogenated to give 1-ethyl-6-(4-methylthiophenyl)-4-oxo-1,4-dihydronicotinic acid, melting point 195°–197° C.

EXAMPLE 14

Preparation of 1-ethyl-6-(4-hydroxyphenyl)-4-oxo-1,4-dihydronicotinic acid

In a manner analogous to that described in Examples 1 and 2, from p-hydroxybenzaldehyde there was obtained 2-(ethylaminomethylene)-5-(4-hydroxyphenyl)-3-oxo-4-pentenoic acid methyl ester, this was cyclized and saponified to give 1-ethyl-6-(4-hydroxyphenyl)-4-oxo-1,4,5,6-tetrahydronicotinic acid and this was subsequently dehydrogenated to give 1-ethyl-6-(4-hydroxyphenyl)-4-oxo-1,4-dihydronicotinic acid, melting point 243°–245° C.

This acid can also be prepared as follows:

3.7 g. of a 50% sodium hydride dispersion are treated in 50 ml. of dimethylformamide (DMF) at room temperature while stirring with 5 g. of ethylmercaptan. Subsequently, there is added thereto a solution of 4.3 g. of 1-ethyl-6-(4-methoxyphenyl)-4-oxo-1,4-dihydronicotinic acid (prepared as described in Example 7) in 15 ml.

of DMF and the mixture is heated to 100° C., a clear solution firstly being obtained. After about 30 minutes, a precipitate is produced. The mixture is stirred at 100° C. for 16 hours, then cooled down and the mixture is taken up in ethyl acetate. The resulting solution is washed neutral with cold 0.1-N hydrochloric acid, dried over sodium sulfate and the solvent is removed. The residue is crystallized from methanol/ether. Yield 3.4 g; melting point 245°–247° C.

EXAMPLE 15

Preparation of 1-ethyl-6-(3-chlorophenyl)-4-oxo-1,4-dihydronicotinic acid

In a manner analogous to that described in Examples 1 and 2, from m-chlorobenzaldehyde there was obtained 2-(ethylaminomethylene)-5-(3-chlorophenyl)-3-oxo-4-pentenoic acid methyl ester, this was cyclized and saponified to give 1-ethyl-6-(3-chlorophenyl)-4-oxo-1,4,5,6-tetrahydronicotinic acid, melting point 143°–145° C., and this was subsequently dehydrogenated to give 1-ethyl-6-(3-chlorophenyl)-4-oxo-1,4-dihydronicotinic acid, melting point 212°–213° C.

EXAMPLE 16

Preparation of 1-ethyl-6-(2,6-dichlorophenyl)-4-oxo-1,4-dihydronicotinic acid

In a manner analogous to that described in Examples 1 and 2, from 2,6-dichlorobenzaldehyde there was obtained 2-(ethylaminomethylene)-5-(2,6-dichlorophenyl)-3-oxo-4-pentenoic acid methyl ester, this was cyclized and saponified to give 1-ethyl-6-(2,6-dichlorophenyl)-4-oxo-1,4,5,6-tetrahydronicotinic acid and this was subsequently dehydrogenated to give 1-ethyl-6-(2,6-dichlorophenyl)-4-oxo-1,4-dihydronicotinic acid, melting point 200°–201° C.

EXAMPLE 17

Preparation of 6-(4-chlorophenyl)-1-methyl-4-oxo-1,4-dihydronicotinic acid

In a manner analogous to that described in Examples 1 and 2, from p-chlorobenzaldehyde there was obtained 5-(4-chlorophenyl)-2-(methylaminomethylene)-3-oxo-4-pentenoic acid methyl ester, melting point 114°–116° C., this was cyclized and saponified to give 6-(4-chlorophenyl)-1-methyl-4-oxo-1,4,5,6-tetrahydronicotinic acid, melting point 205°–206° C., and this was subsequently dehydrogenated to give 6-(4-chlorophenyl)-1-methyl-4-oxo-1,4-dihydronicotinic acid, melting point 275°–280° C. (decomposition).

EXAMPLE 18

Preparation of 1-ethyl-6-(3-methyl-4-methylaminophenyl)-4-oxo-1,4-dihydronicotinic acid In a manner analogous to that described in Examples 1 and 2, from 3-methyl-4-methylamino-benzaldehyde there was obtained 2-(ethylaminomethylene)-5-(3-methyl-4-methylaminophenyl)-3-oxo-4-pentenoic acid methyl ester, this was cyclized and saponified to give 1-ethyl-6-(3-methyl-4-methylaminophenyl)-4-oxo-1,4,5,6-tetrahydronicotinic acid and this was subsequently dehydrogenated to give 1-ethyl-6-(3-methyl-4-methylaminophenyl)-4-oxo-1,4-dihydronicotinic acid, melting point 243°–244° C.

EXAMPLE 19

Preparation of 1-ethyl-4-oxo-6-(3-pyridyl)-1,4-dihydronicotinic acid

In a manner analogous to that described in Examples 1 and 2, from nicotinaldehyde there was obtained 2-(ethylaminomethylene)-3-oxo-5-(3-pyridyl)-4-pentenoic acid methyl ester, melting point 78°–80° C., this was cyclized and saponified to give 1-ethyl-4-oxo-6-(3-pyridyl)-1,4,5,6-tetrahydronicotinic acid, melting point 197°–199° C., and this was subsequently dehydrogenated to give 1-ethyl-4-oxo-6-(3-pyridyl)-1,4-dihydronicotinic acid, melting point 209°–210° C.

1-Ethyl-4-oxo-6-(4-pyridyl)-1,4-dihydronicotinic acid, melting point 268°–270° C., was prepared from isonicotinaldehyde in an analogous manner.

EXAMPLE 20

Preparation of 1-ethyl-6-(4-pyrrolidinophenyl)-4-oxo-1,4-dihydronicotinic acid

In a manner analogous to that described in Examples 1 and 2, from 4-pyrrolidinobenzaldehyde there was obtained 2-(ethylaminomethylene)-3-oxo-5-(4-pyrrolidinophenyl)-4-pentenoic acid methyl ester, this was cyclized and saponified to give 1-ethyl-4-oxo-6-(4-pyrrolidinophenyl)-1,4,5,6-tetrahydronicotinic acid and this was subsequently dehydrogenated to give 1-ethyl-6-(4-pyrrolidinophenyl)-4-oxo-1,4-dihydronicotinic acid, melting point 276°–278° C.

This acid can also be prepared as follows:

7.8 g. of 1-ethyl-4-oxo-6-(4-pyrrolophenyl)-1,4-dihydronicotinic acid methyl ester are hydrogenated at room temperature with 8.5 g. of 5% palladium/carbon in 800 ml. of methanol. After removal of the catalyst, the mixture is evaporated to dryness and the residue is taken up in methylene chloride. The organic solution is extracted with ice-cold 1-N hydrochloric acid, the aqueous extract is neutralized with 1-N sodium hydroxide and extracted with methylene chloride. After drying the solution and evaporation, there are obtained 7.0 g. of 1-ethyl-4-oxo-6-(4-pyrrolidinophenyl)-1,4-dihydronicotinic acid methyl ester having a melting point of 157°–159° C. (from methanol).

The ester can be saponified to the acid in a manner analogous to that described in Example 1.

EXAMPLE 21

Preparation of 1-ethyl-6-(3-aminophenyl)-4-oxo-1,4-dihydronicotinic acid 1.25 g. of 1-ethyl-6-(3-nitrophenyl)-4-oxo-1,4-dihydronicotinic acid in 60 ml. of dimethylformamide were hydrogenated at room temperature for 50 minutes in the presence of 100 mg. of palladium/carbon (5%, w/w). The catalyst was filtered off, the solvent was removed and the residue was crystallized from ethanol/ether. There were obtained 900 mg. of 1-ethyl-6-(3-aminophenyl)-4-oxo-1,4-dihydronicotinic acid having a melting point of 145°–146.5° C.

The following Example illustrates a typical pharmaceutical preparation provided by the present invention.

EXAMPLE A

Tablets weighing 120 mg. or 500 mg. and containing the following ingredients were produced:

| | | |
|---|---|---|
| 1-Ethyl-4-oxo-6-phenyl-1,4-dihydro-nicotinic acid | 10.0 mg. | — |
| 1-Ethyl-6-[4-(dimethylamino)-phenyl]-4-oxo-1,4-dihydronicotinic acid | — | 150 mg. |
| Maize starch | 50.0 mg. | 160 mg. |
| Lactose | 58.0 mg. | 180 mg. |
| Talc | 1.5 mg. | 7 mg. |
| Magnesium stearate | 0.5 mg. | 3 mg. |
| | 120.0 mg. | 500 mg. |

I claim:

1. A compound of the formula

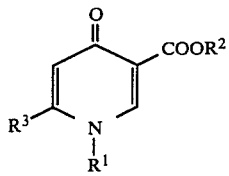

wherein $R^1$ is $C_{1-8}$-alkyl, $C_{3-10}$-cycloalkyl, $C_{3-10}$-cycloalkyl-$C_{1-6}$-alkyl, $C_{1-6}$-alkoxy or $C_{1-6}$-alkoxy-$C_{1-6}$-alkyl; $R^2$ is hydrogen or $C_{1-6}$-alkyl; $R^3$ is phenethyl or styryl, which is substituted by $R^4$, $R^5$ and/or $R^6$; $R^4$ and $R^5$, independently, are halogen, trifluoromethyl, hydroxy, $C_{1-6}$-alkoxy, $C_{1-6}$-alkylthio, $C_{1-6}$-alkyl, amino, acylamino, $C_{1-6}$-alkylamino, di-$C_{1-6}$-alkylamino, nitro or a 5-membered or 6-membered heterocycle linked via ring N- or C-atom or $R^4$ and $R^5$ taken together are $C_{1-6}$-alkylenedioxy; $R^6$ is $C_{1-6}$-alkoxy, or a pharmaceutically acceptable salt thereof.

2. The compound of claim 1 wherein $R^3$ is a substituted styryl group.

3. The compound of claim 2 wherein said compound is 1-ethyl-6-(p-methoxystyryl)-4-oxo-1,4-dihydronicotinic acid.

4. The compound of claim 1 wherein $R^3$ is a substituted phenethyl group.

5. A pharmaceutical composition comprising a compound of the formula

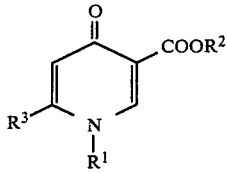

wherein $R^1$ is $C_{1-8}$-alkyl, $C_{3-10}$-cycloalkyl, $C_{3-10}$-cycloalkyl-$C_{1-6}$-alkyl, $C_{1-6}$-alkoxy or $C_{1-6}$-alkoxy-$C_{1-6}$-alkyl; $R^2$ is hydrogen or $C_{1-6}$-alkyl; $R^3$ is phenethyl or styryl, which is substituted by $R^4$, $R^5$ and/or $R^6$; $R^4$ and $R^5$, independently, are halogen, trifluoromethyl, hydroxy, $C_{1-6}$-alkoxy, $C_{1-6}$-alkylthio, $C_{1-6}$-alkyl, amino, acylamino, $C_{1-6}$-alkylamino, di-$C_{1-6}$-alkylamino, nitro or a 5-membered or 6-membered heterocycle linked via ring N- or C-atom or $R^4$ and $R^5$ taken together are $C_{1-6}$-alkylenedioxy; $R^6$ is $C_{1-6}$-alkoxy, or a pharmaceutically acceptable salt thereof and a carrier material.

* * * * *